United States Patent [19]
Prahl

[11] Patent Number: 4,892,553
[45] Date of Patent: Jan. 9, 1990

[54] ARTIFICIAL FOOT FOR A LEG PROSTHESIS

[75] Inventor: Gregor M. Prahl, Rullstorf, Fed. Rep. of Germany

[73] Assignee: IPOS GmbH & Co, KG, Lüneburg, Fed. Rep. of Germany

[21] Appl. No.: 205,462

[22] Filed: Jun. 10, 1988

[30] Foreign Application Priority Data

Mar. 29, 1988 [DE] Fed. Rep. of Germany ... 8804228[U]

[51] Int. Cl.<sup>4</sup> .............................................. A61F 2/66
[52] U.S. Cl. ..................................................... 623/55
[58] Field of Search .................................... 623/47-56

[56] References Cited

U.S. PATENT DOCUMENTS

| | | | |
|---|---|---|---|
| 1,219,374 | 3/1917 | Carrico | 623/55 |
| 3,484,871 | 12/1969 | Orange | 623/55 |
| 3,890,650 | 6/1975 | Prahl | 623/55 |
| 3,920,610 | 11/1975 | Wagner | 623/55 |
| 4,177,525 | 12/1979 | Arbogast et al. | 623/55 |
| 4,645,509 | 2/1987 | Poggi et al. | 623/55 |
| 4,721,510 | 1/1988 | Cooper et al. | 623/55 |

*Primary Examiner*—V. Millin
*Assistant Examiner*—James Prizant
*Attorney, Agent, or Firm*—Toren, McGeady & Associates

[57] ABSTRACT

Within its plantar area the artificial foot for a leg prosthesis is provided—embedded within the molded foot portion—with a plate-shaped reinforcing member (10) that consists of two superposed leaf springs (10a, 10b) of approximately equal length which are configured so as to conform to the rolling profile of the foot, as a result whereof an improved metatarsal elasticity is obtained.

13 Claims, 2 Drawing Sheets

ARTIFICIAL FOOT FOR A LEG PROSTHESIS

BACKGROUND OF THE INVENTION

The present invention relates to an artificial foot for a leg prosthesis comprising a foamed plastic moulded foot portion with a plate-shaped, metallic reinforcing member embedded within its plantar area which, in the ball area, is constructed with a curved section extending in the manner of a ball of the foot for supporting the rolling function of the foot and with - serving in each case as an elastic, yielding cushioning - a forefoot core and a function core consisting of a tongue disposed within the heel area, the function core and the reinforcing member being rigidly interconnected. Polyurethane foamed plastic which possesses the advantage of a light weight has been employed for artificial feet for a long time.

In order to enable the artificial foot to approximately perform the function given in a natural foot, by way of example, in U.S. Pat No. 3,335,428, a leg prosthesis foot portion has been proposed that is constructed of elastic plastics of varying hardnesses.

In addition, from the DE-PS No. 354 246, an artificial foot is known in which, within the plantar area of said artificial foot, a metal bar is embedded. This artificial foot is intended to enable a foot or a leg amputee to take long strides, since taking of long steps involves the oblique rearward displacement of the lower leg, that is to say the yielding of the heel of the foot which rests on the ground with its entire base. It is intended, moreover, to bring about the easy straightening up again of the lower leg without the same exceeding the vertical position, while the forward displacement of the body weight and the raising of the heel is intended to be rendered possible by the normal flaxibility of the metatarsal and dactylar section of the artificial foot. This flexibility is intended to be obtained by embedding a spring plate extending through the plantar and the heel sections. In order to now produce the oblique rearward projection of the lower leg, this known embodiment of an artificial foot provides a connection between the rigid lower leg and the spring plate in which the sailient portion, from its upright position, moves rearwardly in the fashion of a rocker and, when the body weight is moved in the forward direction, again assumes the first position. This rocking motion is effected in that the rigid lower leg which tapers in a wedge-like manner, is seated in a saddle, the one slope of which is formed by the instep of the artificial foot and its counterslope by a branch of the spring plate. For additional cushioning, a compressible wedge-type cushion, e.g. of soft rubber, is disposed between the branch and the spring plate proper. In order to prevent any undesirable noise being produced when the front wedge surface on the salient portion impinges upon the foot, the forefoot or the metatarsus consists of a pliant or readily compressible, at any rate noise-deadening material, preferably felt. The abutment surface of the lower leg is also covered with this material. In this artificial foot, the branch of the spring plate is rigidly connected to the rear wedge surface of the lower leg. In this case, however, the branch is not bent sharply because a rocking or swaying motion is aimed at. For this reason it is attached to the plate so as to glide with its bend.

In this artificial foot, a steel spring with resilient properties is thus inserted which extends as far as to the forefoot. However, from a constructional point of view, the most important differences in elasticity between the metatarsus and the forefoot have not been taken into account in this case. However, the steel spring employed does not render a natural rolling function possible, moreover, the connection problems between the various materials are not solved in the elastic sphere. Furthermore, from the DE-PS No. 361 972, an aritficial foot is known which is provided with a longitudinal spring cushioning means consisting of several leaf springs arranged in steps relative to one another, the leaf springs of which are secured with their rear extremities to the underside of a rigid block forming the rear foot portion which, however, is separated from the sole of the foot by an intermediate layer, while the spring front extremities which are run downwardly in a suitable double curveature, press directly upon the sole which is expediently covered with a protective plate. In this artificial foot, too, an attempt is made to control the movements of the foot by means of a metal spring; but it does not allow any mobility within the metatarsophalangeal area.

In an artificial foot for leg prostheses known from the U.S. Pat. NO. 2,556,525, a rigid, but flexible plastic member is inserted into an outer foamed plastics moulded foot portion, said member extending over the entire length of the foot, a metal insert of spring steel being embedded in this rigid but nevertheless flexible plastic member. Even if an internal, partly flexible plastic member with a metal insert of spring steel is used in this known artificial foot, it is not possible with this artificial foot to place the rolling function of the foot onto the division-by-three line provided by nature. For the rest, the metal insert is also run as far as to the point of the foot. In spite of the use of a flexible plastic member and of a metal insert fabricated from spring steel, an adequate mobility within the metatarsophalangeal joint, as exists in nature, is not possible. The important bending in the metatarsophalangeal joint has not been taken into consideration in this known embodiment and, due to the structural configurations, is not possible either.

In order to provide an artificial foot for leg prostheses with a rolling resistance of high elasticity and a facility for bending in the metatarsophalangeal joint for a relatively long period, in the DE-PS No. 23 41 887, the artificial foot described in the beginning has been proposed. In this artificial foot the forefoot elasticity is ensured by the use of a homogenous Vulkollan (elastomer) member, that is to say, a resilience is taken into consideration in the forefoot which exceeded the cushioning effects produced until then. It is true that up till now it had not been possible to functionally utilize the advantages provided by this resilience in its physical influence factor on the gait or walk image.

It therefore is the object of the present invention to develop the artificial foot stated in the beginning in such a way that a substantial degree of metatarsal elasticity is ensured up to a maximum rolling moment of 120 Nm even at a continuous stress of up to 3 million load alternations without having to forego the advantages offered by the artificial foot known from the DE-PS No. 23 41 887.

SUMMARY OF THE INVENTION

This technical problem is solved in that the reinforcing member consists of at least two superposed leaf springs of approximately equal length which are configured in accordance with the rolling profile of the foot.

Advantageously, this artificial foot possesses a significant degree of mobility in the metatarsophalageal joint, an elastic, yielding cushioning both in the forefoot as well as in the heel area, the rolling resistance being invariably predetermined for a relatively long period. Over and above that, a simple adaption to varying heel heights is possible and a maximum degree of wearing comfort is ensured for the wearer of the artificial foot without any readjustment operations becoming necessary for maintaining a uniform rolling function of the foot. By supporting the metallic reinforcing member in the heel section of the moulded foot portion, an increased strength of the foot portion is achieved without any impairment of the requisite elastic and yielding cushioning means in the forefoot and heel area. The simple adaption to varying heel heights is possible without difficulty merely by changing the tab arranged within the heel portion of the moulded foot portion without it being necessary for this purpose to alter the entire function core in order to achieve an adaptation to varying heel heights.

In particular, the construction according to the invention makes it possible that, by the resiliently constructed forefoot and metatarsal areas, kinetic energy is absorbed, stored and, when removing the load from the rearward position of the step, is once more inputted into the prosthesis as released energy. This feedback of released kinetic energy into the prosthetic systems demonstrably results in an obvious energy relief during the locomotion of the patient. It is furthermore possible now to dispense with ankle joints in the artificial foot, whereby a loss of energy arising in the joints due to friction is avoided and the stored energy can be rendered fully utilizable again as feedback. In both the forefoot and in the metatarsal area, the artificial foot is highly resilient and capable of absorbing a maximum rolling moment of 120 Nm. This maximum rolling load also determines the dimensioning of the springs.

Further developments of the invention are described in the Subclaims 2 thru 11.

Particular emphasis has to be laid here on the highly resilient effect of the leaf springs acting as double leaf springs fabricated from titanium, a high-tensile titanium-aluminum alloy or from a suitable material preferably possessing the same properties as titanium which, according to a further development of the invention, prevents a contacting of the respective leaf spring surfaces with the aid of the spacer interposed therebetween. The spacer preferably consists of high-molecular polyethylene or some other suitable plastic material and acts as a noise-deadening gliding layer for controlling the maximum elastic force to be absorbed.

BRIEF DESCRIPTION OF THE DRAWINGS

An embodiment of the invention will be explained with the aid of the following drawings.

DETAILED DESCRIPTION OF THE PREFERRED EMBODIMENT

Figure 1:
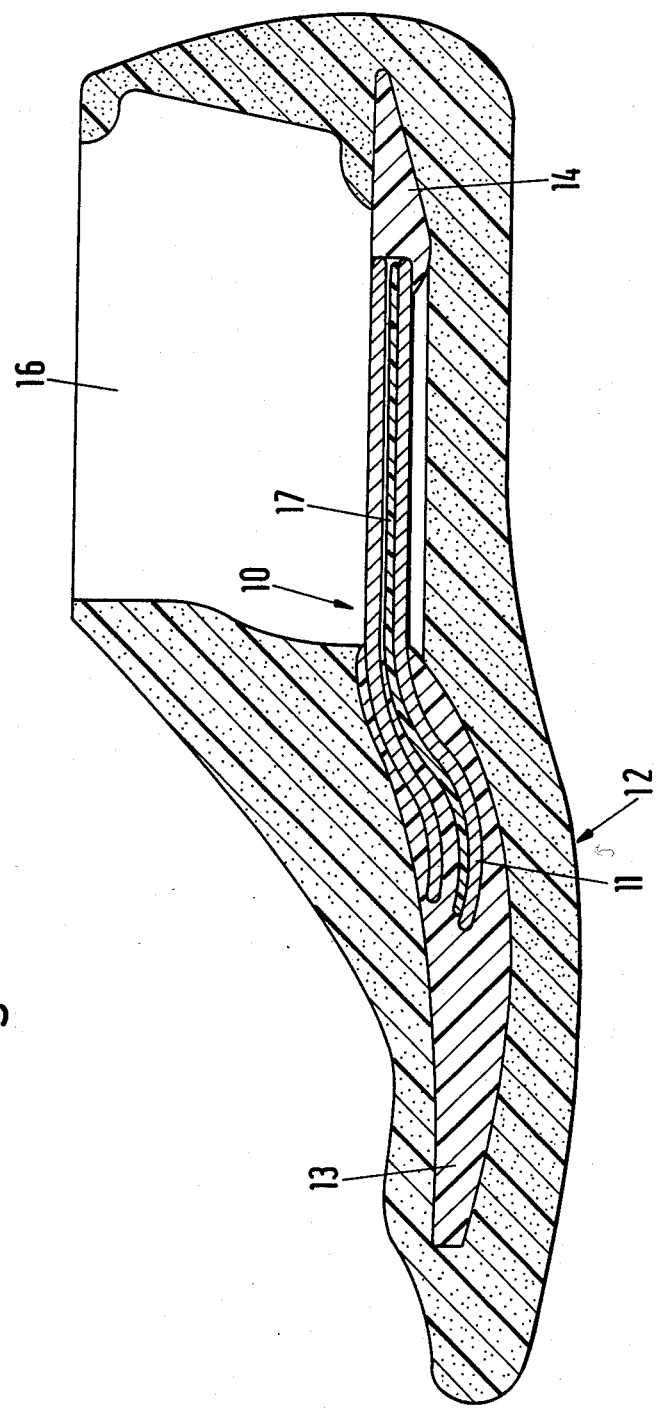
FIG. 1 shows a section through the artificial foot.

The reinforcing member 10 shown in the FIG. 1 is provided with a downwardly directed curved section 11 within the ball area 12 of the artificial foot which is shaped in accordance with the rolling profile of the foot. The reinforcing member 10 is embedded within a forefoot core 13 in the same way as within a tab 14 located in the heel area. The function core consisting of the parts 10, 13 and 14 is embedded in a foamed plastic foot portion 15 which, in its rearward section, has a cavity 16 which is run up to the reinforcing member 10 and in which joints or rigid attachment means can be screwed directly onto the reinforcing member 10.

The downwardly directed curved section 11 is constructed in such a fashion that the rolling function is placed onto the front division-by-three line (metatarsophalangeal joint line) predetermined by nature. At the same time, a forefoot core 13 consisting of an elastomer is vulcanized onto the curved section 11 of reinforcing member 10 which, in its terminating line, corresponds to the outer shape of the ball of the foot. Due to a foam-embedded structure this forefoot core 13 is absolutely resistant to aging so that the rolling resistance can invariably be predetermined for relatively long periods. In the same way, within the heel area, a tab 14, likewise consisting of an elastomer, is attached by vulcanization in order to strengthen the reinforcing member 10.

Figure 2:
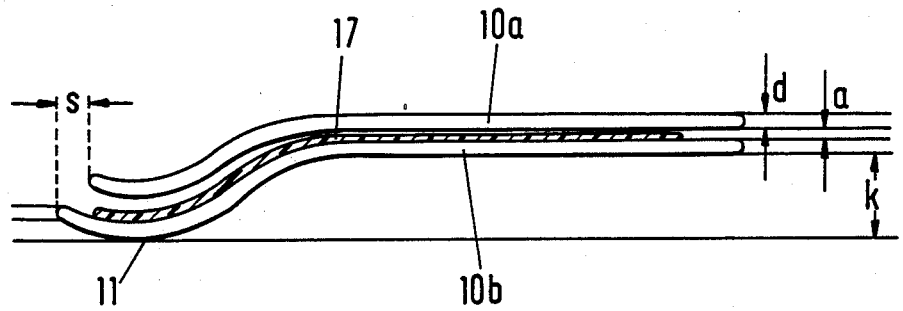
FIG. 2 shows a side elevation of the reinforcing member consisting of two leaf springs.
Figure 3:
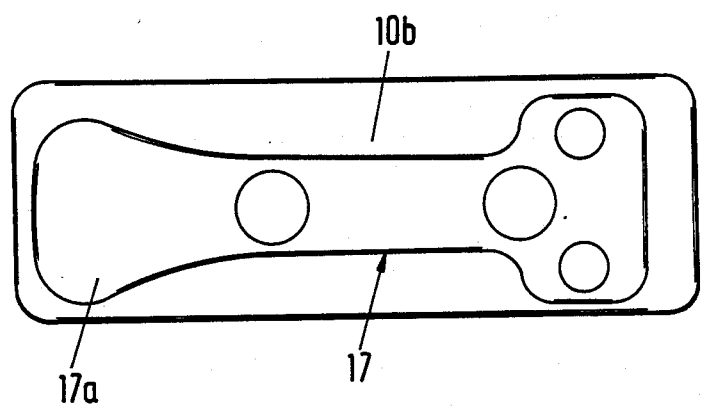
FIG. 3 shows a top view of the bottom leaf spring with a spacer placed thereupon.

The construction of the reinforcing member 10 being of particular relevance to the invention appears in detail from the FIGS. 2 and 3. In this case the metatarsus construction consists of two leaf springs 10a and 10b of approximately equal length which, in a superposed arrangement, possess the already described design of the reinforcing member 10. It is also possible for more leaf springs than two to be used. Within the right-hand area, the leaf springs 10a and 10b are constructed in a parallelly extending plane fashion, a spacer fabricated from polyethylene or some other suitable material being disposed therebetween prevents a contact between the surfaces of the leaf springs 10a, 10b.

Within the right-hand area (FIG. 3), the spacer possesses essentially a T-shaped configuration, as a consequence of which its salient portion aligned with the forefoot undergoes a lingulate broadening, preferably in such a way that the leaf springs 10a and 10b overlap the spacer 17 on all sides.

If several leaf springs are combined for forming the reinforcing member 10, then one spacer 17 each is disposed between every two leaf springs.

It is the special function of the spacer to act as a noisedeadening gliding layer, by the thickness of which the elastic force to be maximally absorbed can be controlled. The further spaced apart the leaf springs 10a and 10b are, the greater will be the maximum stability under load of the artificial foot.

Toward the front portion, that is to say on the left-hand side in the FIGS. 2 and 3, a leaf spring gap becoming progressively wider is achieved by the curved section corresponding to the rolling shape of the artificial foot. On the front side, the bottom spring 10b overlaps the top leaf spring 10a by a distance s of approximately 5 mm. The leaf spring arrangement depicted in the FIGS. 2 and 3 with interposed spacer is potted in a mold depending on the size of the foot and the side of the foot so as to become a homogeneous functional component. Care is taken in this operation that the elasticity of the forefoot and that of the metatarsus pass smoothly into one another.

In order to attain the excellent gliding property of the spacer 17, the spacer may also consist of polyurethane, particularly a cross-linked polyurethane elastomer known by the trade name "Vukollan". Polyurethane possesses a high abrasion resistance so that a constant rolling effect is ensured at all times. Added to this is the great and independent capability of returning from a deformed position into the starting position. The foot core 13 and the tab 14 likewise consist of polyurethane, in particular a cross-linked polyurethane elastomer that is known by its trade name of "Vulkollan". Polyurethanes which are obtained by the conversion of diisocyanates known by the trade name of "Desmodur", according to the polyisocyanate-polyaddition process, may also be employed. TDI, MDI and HDI are types of isocyanate used frequently in this connection. For strongly cross-linked polyurethanes, above all triisocyanates and, inter alia, also polyisocyanates are made use of. Here, too, the property of a high gliding capability is expolited.

By the difference in the flexural rate of the top and the bottom leaf spring 10a, 10b, respectively, existing within the area of the curved section, the horizontal displacements of the two spring members are compensated by the widening elastomer proportion (polyurethane) of the spacer 17.

The residual gap existing circumferentially around the spacer 17 passes into the polyurethane, i.e. between the two leaf springs 10a and 10b, which coalesce with the polyurethane with the aid of special primers, an elastic connection comes into existence which, by the distance k between the rear leaf spring plane and the curved section 11, renders possible spring paths or deflections on the front load portion of more than 15 mm in the rolling point. These relatively substantial spring paths render the use of joints partly superfluous due to their functionally substantial dorsal flexion. At the same time, a large area of energy being released is developed by the spring-back resilience which can be fed back again into the prosthetic system.

With a minimum of weight the leaf spring structure is capable of coping permanently with a high rolling stress, it functions with complete silence and distinguishes itself by large spring paths. Due to the high-tensile titanium alloy selected for the leaf springs in conjunction with polyurethane, in which the leaf spring construction is embedded, the artificial foot according to the invention is by far superior to other leaf spring constructions such as are known within the field of carbon fiber-reinforced systems. In particular, in constructions known according to the prior art, such large spring paths have not been possible up till now.

What is claimed is:

1. An artificial foot for a leg prosthesis comprising a foamed plastic molded foot portion having a ball and plantar area with a plate-shaped, metallic reinforcing member embedded therein which has a section curved so as to extend correspondingly to the ball of the foot so as to support a rolling function of the foot, and an elastic, yielding cushioning forefoot core and a function core consisting of a tab disposed within a heel area, the function core and the reinforcing member being rigidly interconnected, the reinforcing member including at least two superimposed leaf springs of approximately equal length configured to correspond with the rolling profile of the foot, the leaf springs consisting of one of titanium and a high-tensile titanium-aluminum alloy, the at least two leaf springs including a bottom leaf spring and a top leaf spring, the bottom leaf spring being provided so as to overlap the top leaf spring by at least 5 mm in the direction of the point of the foot; wherein said artificial foot further comprises an elastic spacer disposed between the leaf springs, the elastic spacer being fabricated from a material possessing a high gliding ability and being essentially T-shaped with a salient portion directed toward the point of the foot which becomes under so as to assume a lingulate configuration so that the leaf springs overlap the spacer on all sides.

2. An artificial foot according to claim 1, wherein the leaf springs are of equal thickness.

3. An artificial foot according to claim 1, wherein the leaf springs, in a top view projection, are essentially rectangular, having rounded-off corners and edges.

4. An artificial foot according to claim 1, wherein the leaf springs are spaced from one another by a spacing of at least 1 mm, which spacing increases toward the point of the foot.

5. An artificial foot according to claim 1 wherein the spacer within the heel area, has a thickness of 1 mm and, toward the point of the foot, a thickness of 3.5 mm to 4.5 mm.

6. An artificial foot according to claim 1, wherein the leaf springs are embedded within the foot core and the tab, both of which consist of polyurethane.

7. An artificial foot according to claim 1, wherein the leaf springs are essentially planar from the heel area up to a metatarsal area, the curved section within the ball area extending at least 15 mm deeper than the leaf springs.

8. An artificial foot according to claim 2, wherein the leaf springs have a thickness of 2.7 mm.

9. An artificial foot according to claim 1, wherein the material of the elastic spacer is a high-molecular polyethylene.

10. An artificial foot according to claim 4, wherein the spacing increases toward the point of the foot to more than 3.5 mm.

11. An artificial foot according to claim 10, wherein the spacing increases to between 3.5 mm and 4 mm.

12. An artificial foot according to claim 6, wherein the polyurethane is a cross-linked polyurethane elastomer.

13. An artificial foot according to claim 7, wherein the curved section extends 16 mm to 21 mm deeper.

* * * * *